United States Patent
Keränen (10) Patent No.: US 9,526,614 B2
(45) Date of Patent: Dec. 27, 2016

(54) SYSTEM FOR IMPROVING THE FUNCTION OF A HEART VALVE

(75) Inventor: Olli Keränen, Bjärred (SE)

(73) Assignee: Medtentia International Ltd. Oy, Helsinki (FI)

(*) Notice: Subject to any disclaimer, the term of this patent is extended or adjusted under 35 U.S.C. 154(b) by 761 days.

(21) Appl. No.: 12/850,539

(22) Filed: Aug. 4, 2010

(65) Prior Publication Data

US 2010/0318183 A1  Dec. 16, 2010

Related U.S. Application Data

(63) Continuation of application No. 11/885,116, filed as application No. PCT/SE2006/000251 on Feb. 27, 2006, now Pat. No. 9,180,006.

(60) Provisional application No. 60/704,417, filed on Aug. 2, 2005.

(30) Foreign Application Priority Data

Feb. 28, 2005  (SE) ........................................ 0500440

(51) Int. Cl.
*A61F 2/24* (2006.01)

(52) U.S. Cl.
CPC .............. *A61F 2/2448* (2013.01); *A61F 2/246* (2013.01); *A61F 2/2442* (2013.01); *A61F 2/2445* (2013.01); *A61F 2/2466* (2013.01); *A61F 2210/009* (2013.01); *A61F 2210/0014* (2013.01); *A61F 2220/0016* (2013.01); *A61F 2220/0033* (2013.01); *A61F 2220/0041* (2013.01); *A61F 2220/0075* (2013.01); *A61F 2220/0083* (2013.01); *A61F 2230/0006* (2013.01); *A61F 2230/0013* (2013.01); *A61F 2230/0091* (2013.01)

(58) Field of Classification Search
CPC .................. A61F 2/2442–2/2448; A61F 2/246
USPC ....................................... 623/1.22, 2.36–2.37
See application file for complete search history.

(56) References Cited

U.S. PATENT DOCUMENTS

| | | |
|---|---|---|
| 4,042,979 A | 8/1977 | Angell |
| 5,290,300 A | 3/1994 | Cosgrove et al. |
| 5,403,305 A | 4/1995 | Sauter et al. |
| 6,217,610 B1 | 4/2001 | Carpentier et al. |

(Continued)

FOREIGN PATENT DOCUMENTS

| | | |
|---|---|---|
| WO | WO 99/04730 A1 | 2/1999 |
| WO | WO 03/105730 A1 | 12/2003 |

(Continued)

OTHER PUBLICATIONS

WIPO, International Search Report PCT/ISA/210 in PCT/SE2006/000251 dated May 31, 2006.

(Continued)

*Primary Examiner* — Yashita Sharma
*Assistant Examiner* — Rebecca Preston
(74) *Attorney, Agent, or Firm* — Inskeep IP Group, Inc.

(57) ABSTRACT

A device for improving the function of a heart valve comprises a first loop-shaped support, which is configured to abut a first side of the heart valve, and a second loop-shaped support, which is configured to abut a second side of the heart valve opposite to said first side, whereby a portion of the valve tissue is trapped between the first and second supports. An outer boundary of the second support is greater than an outer boundary of the first support.

13 Claims, 6 Drawing Sheets

(56) References Cited

U.S. PATENT DOCUMENTS

| | | | |
|---|---|---|---|
| 6,258,117 | B1 | 7/2001 | Camrud et al. |
| 6,368,348 | B1 | 4/2002 | Gabbay |
| 6,406,493 | B1 | 6/2002 | Tu et al. |
| 6,419,696 | B1 | 7/2002 | Ortiz et al. |
| 6,585,767 | B1 | 7/2003 | Holley et al. |
| 6,602,289 | B1 | 8/2003 | Colvin et al. |
| 6,723,038 | B1 | 4/2004 | Schroeder et al. |
| 7,077,861 | B2 | 7/2006 | Spence |
| 7,186,265 | B2* | 3/2007 | Sharkawy et al. ........... 623/2.38 |
| 2001/0021874 | A1 | 9/2001 | Carpentier et al. |
| 2002/0013621 | A1 | 1/2002 | Stobie et al. |
| 2002/0173841 | A1* | 11/2002 | Ortiz et al. .................. 623/2.11 |
| 2003/0045929 | A1 | 3/2003 | McCarthy et al. |
| 2003/0069593 | A1* | 4/2003 | Tremulis et al. ............. 606/142 |
| 2003/0199975 | A1 | 10/2003 | Gabbay |
| 2004/0019357 | A1 | 1/2004 | Campbell et al. |
| 2004/0106989 | A1* | 6/2004 | Wilson et al. ................ 623/2.11 |
| 2004/0127981 | A1 | 7/2004 | Rahdert et al. |
| 2004/0138745 | A1 | 7/2004 | Macoviak et al. |
| 2004/0148021 | A1 | 7/2004 | Cartledge et al. |
| 2004/0162611 | A1 | 8/2004 | Marquez |
| 2004/0167620 | A1 | 8/2004 | Ortiz et al. |
| 2004/0220593 | A1 | 11/2004 | Greenhalgh |
| 2004/0243230 | A1 | 12/2004 | Navia et al. |
| 2004/0260393 | A1 | 12/2004 | Rahdert et al. |
| 2005/0010275 | A1* | 1/2005 | Sahatjian et al. ............ 623/1.11 |
| 2005/0119734 | A1* | 6/2005 | Spence et al. ................ 623/2.11 |
| 2005/0149114 | A1 | 7/2005 | Cartledge et al. |
| 2005/0149178 | A1 | 7/2005 | Spence |
| 2005/0288777 | A1 | 12/2005 | Rhee et al. |
| 2005/0288781 | A1* | 12/2005 | Moaddeb et al. ........... 623/2.37 |

FOREIGN PATENT DOCUMENTS

| | | | |
|---|---|---|---|
| WO | WO 2004/089250 | A1 | 10/2004 |
| WO | WO 2005/039452 | A1 | 5/2005 |
| WO | WO 2006/054930 | A1 | 5/2006 |
| WO | WO 2006/091163 | A1 | 8/2006 |
| WO | WO 2006/093656 | A1 | 9/2006 |
| WO | WO 2007/030063 | A1 | 3/2007 |

OTHER PUBLICATIONS

WIPO, Patent Family Annex PCT/ISA/201 re SE 05/00109 dated Sep. 7, 2005.
PCT Request Form PCT/RO/101 filed in PCT/SE2006/000251 on Feb. 27, 2006.
WIPO, PCT Form PCT/IB/306 Notification of Recording of a Change in PCT/SE2006/000251 dated Jan. 11, 2007.
WIPO, PCT Form PCT/IB/308 in PCT/SE2006/000251 dated Sep. 28, 2006.
International Preliminary Report on Patentability dated Sep. 11, 2007.
Written Opinion of the International Searching Authority dated Jun. 2, 2006.
United States Patent and Trademark Office, Notice of Allowance mailed Jan. 24, 2001 in U.S. Appl. No. 11/667,335, 8 pages.
United States Patent and Trademark Office, Office Action mailed Dec. 10, 2010 in U.S. Appl. No. 12/850,539, 12 pages.
United States Patent and Trademark Office, Office Action mailed Sep. 16, 2010 in U.S. Appl. No. 12/065,884, 12 pages.
United States Patent and Trademark Office, Final Office Action mailed Aug. 20, 2010 in U.S. Appl. No. 11/885,116, 8 pages.
United States Patent and Trademark Office, Office Action mailed May 7, 2010 in U.S. Appl. No. 11/667,335, 18 pages.
United States Patent and Trademark Office, Office Action mailed Mar. 5, 2010 in U.S. Appl. No. 11/885,116, 6 pages.
United States Patent and Trademark Office, Final Office Action mailed Feb. 16, 2011 in U.S. Appl. No. 11/793,028, 10 pages.
United States Patent and Trademark Office, Office Action mailed Jun. 8, 2009 in U.S. Appl. No. 11/793,028, 20 pages.
United States Patent and Trademark Office, Office Action mailed May 26, 2009 in U.S. Appl. No. 11/885,116, 16 pages.
WIPO, International Preliminary Examining Authority, International Preliminary Report on Patentability mailed Sep. 11, 2007 in International Patent Application No. PCT/SE2006/000251, 1 page.
WIPO, Swedish International Preliminary Examining Authority, Written Opinion mailed Jun. 2, 2006 in International Patent Application No. PCT/SE2006/00251, 7 pages.
WIPO, Swedish International Preliminary Examining Authority, Written Opinion mailed Mar. 1, 2006 in International Patent Application No. PCT/SE2005/000909, 6 pages.
WIPO, Swedish International Search Authority, International Search Report mailed Jun. 2, 2006 in International Patent Application No. PCT/SE2006/000251, 5 pages.
WIPO, Swedish International Search Authority, International Search Report mailed Mar. 1, 2006 in International Patent Application No. PCT/SE2005/000909, 6 pages.
Medtentia AB, PCT Request filed Feb. 2, 2006 in International Patent Application No. PCT/SE2006/000251, 4 pages.

* cited by examiner

SYSTEM FOR IMPROVING THE FUNCTION OF A HEART VALVE

RELATED APPLICATIONS

This application is a continuation of and claims priority to U.S. patent application Ser. No. 11/885,116 filed Apr. 4, 2008, now U.S. Pat. No. 9,180,006, entitled Devices And A Kit For Improving The Function Of A Heart Valve, which claims priority to International Patent Application No. PCT/SE06/00251, International Filing Date Feb. 27, 2006, entitled Devices And A Kit For Improving The Function Of A Heart Valve, and to U.S. Provisional Application Ser. No. 60/704,417 filed Aug. 2, 2005 entitled Device For Improving Function Of Heart Valve, all of which are hereby incorporated herein by reference in their entireties.

FIELD OF THE INVENTION

The present invention generally relates to heart valve repair techniques and annuloplasty devices. More specifically, the invention relates to the repair of heart valves having various malformations and dysfunctions.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak (insufficiency). The leaflets and chords may become calcified and thickened rendering them stenotic (obstructing forward flow). Finally, the valve relies on insertion of the chordae inside the ventricle. If the ventricle changes in shape, the valve support may become non-functional and the valve may leak.

Mitral and tricuspid valve replacement and repair are traditionally performed with a suture technique. During valve replacement, sutures are spaced around the annulus (the point where the valve leaflet attaches to the heart) and then the sutures are attached to a prosthetic valve. The valve is lowered into position and when the sutures are tied, the valve is fastened to the annulus. The surgeon may remove all or part of the valve leaflets before inserting the prosthetic valve. In valve repair, a diseased valve is left in situ and surgical procedures are performed to restore its function. Frequently an annuloplasty ring is used to reduce the size of the annulus. The ring serves to reduce the diameter of the annulus and allow the leaflets to oppose each other normally. Sutures are used to attach a prosthetic ring to the annulus and to assist in plicating the annulus.

In general, the annuloplasty rings and replacement valves must be sutured to the valve annulus and this is time consuming and tedious. If the ring is severely malpositioned, then the stitches must be removed and the ring repositioned relative to the valve annulus during restitching. In other cases, a less than optimum annuloplasty may be tolerated by the surgeon rather than lengthening the time of the surgery to restitch the ring.

During heart surgery, a premium is placed on reducing the amount of time used to replace and repair valves as the heart is frequently arrested and without perfusion. It would therefore be very useful to have a method to efficiently attach a prosthesis into the mitral or tricuspid valve position.

In U.S. Pat. No. 6,419,696, an annuloplasty device is disclosed. The annuloplasty device comprises a first and a second support ring, which are connected to each other to form a coiled configuration. The first and second support rings are arranged to abut opposite sides of a valve annulus to trap valve tissue therebetween. This annuloplasty device may be easily applied to the valve by rotating the device into position on opposite sides of the valve annulus.

SUMMARY OF THE INVENTION

It is an object of the invention to provide an improved valve repair. It is a specific object of the invention to provide an annuloplasty device, which provides a lessened risk for rupture of valve leaflets when applied to the heart valve.

These and other objects of the invention are accomplished by means of devices according to the independent claims. Preferred embodiments of the invention are apparent from the dependent claims.

According to a first aspect of the invention, there is provided a device for improving the function of a heart valve comprised of valve tissue including an annulus and a plurality of leaflets. The device comprises a first loop-shaped support, which is configured to abut a first side of the heart valve, and a second loop-shaped support, which is configured to abut a second side of the heart valve opposite to said first side, whereby a portion of the valve tissue is trapped between the first and second supports, wherein an outer boundary of the second support is greater than an outer boundary of the first support.

This device may be used to perform annuloplasty, that is to reshape the valve annulus, in order to improve the function of the valve. The first and second loop-shaped supports are to be positioned on opposite sides of the heart valve and trap valve tissue therebetween to fixate a desired shape of the valve. The device may also be used to carry and position a replacement heart valve.

The feature that the outer boundary of the second support is greater than the outer boundary of the first support implies that the device, when properly positioned at a heart valve, may be arranged such that the first and second loop-shaped supports are displaced to one another on the opposite sides of the heart valve. It has been found that this arrangement diminishes a risk that a rupture is created in the leaflets, which during normal heart action bends over the lower support to open the valve. A possible explanation for this diminished rupture risk is that since the supports are displaced to one another, the pinch between the first and second supports does not sharply define a radial position in which the leaflets of the valve bend over the lower support. When using the device on an atrial valve, the lower support may now be arranged close to the annulus of the valve, which is larger on its ventricular side. Thereby, the device may also be arranged to minimally affect the movement of the leaflets during normal heart action. Further, a large lower support provides a possibility to move the support around the chords in the left ventricle during insertion of the device. However, it is conceivable that the diminished rupture risk may be achieved by instead making the outer boundary of the upper support greater than the outer boundary of the lower support.

As used herein, the term "loop-shaped" should be construed as a curved shape that may be closed as a ring with a circular, elliptic, or D-shaped form or any other closed form which may fit the shape of the valve annulus. The term "loop-shaped" also includes a curved shape that is open forming an arcuate shape, such as a C-shape or U-shape, which includes an angular turn of at least 180° such that the support may abut valve tissue along a major part of the annular valve shape. The term "loop-shaped" also includes a curved shape overlapping itself to form a portion of a coil.

The first and the second loop-shaped supports may be separate entities and may be arranged to be connected when inserted in engagement with valve tissue.

Alternatively, an end of the first loop-shaped support may be connected to an end of the second loop-shaped support through a connecting part, whereby the supports and the connecting part form a coil-shape.

This implies that the first and second supports may be simultaneously applied in position at the heart valve. When used for an atrial valve, the coil-shape may be applied from the atrial side at a commissure between the leaflets of the atrial valve and be rotated 360° such that one loop-shaped support is inserted through the commissure to extend along the valve on its ventricular side and the other loop-shaped support is arranged along the valve on its atrial side.

The connecting part may be releasably attached to the first and second loop-shaped supports for disconnecting the end of the first loop-shaped support from the end of the second loop-shaped support after insertion to the heart valve.

This implies that the device may be placed in abutment with the heart valve without having any part extending through the opening of the heart valve. Thus, the first and second supports may separately be arranged in abutment with valve tissue such that each support may over time grow into the valve tissue. As a result, the device does not present any surface of foreign material that may cause blood clot forming or tissue overgrowth in the opening of the heart valve.

The first loop-shaped support may be continuous with the second loop-shaped support to form a coil-shaped member. This implies that the device has a simple design comprising a single coil-shaped part, which may easily be positioned in a heart valve by rotating the coil-shaped member such that the loop-shaped supports are arranged on opposite sides of the valve.

An end portion of the coil-shaped member may be bent such that the end portion has a greater pitch than the rest of the coil-shaped member. This is especially advantageous when using the device to treat an atrial valve. When rotating the coil-shaped member for positioning the device, a greater pitch of the leading end of the coil-shaped member entering the ventricle implies that a risk that the coil-shaped member gets stuck in the chords during insertion is reduced.

The second support may have a round cross-section. The first support may also have a round cross-section. This implies that a rounded edge is presented to the valve tissue being trapped, whereby a risk that a rupture is created in the leaflets is further diminished.

The first and second supports may have equal shapes, wherein the second support is in larger scale than the first support. This implies that the relationship between the first and second support is equal over the entire valve. As a result, the pinch between the first and second supports is constant over the entire valve.

The outer boundary of the first support may be larger than an inner boundary of the second support. This implies that the supports overlap somewhat, whereby the pinch between the supports certainly is sufficiently strong to maintain a remodelled shape of the heart valve.

Preferably, the outer boundary of the first support corresponds to a curve through the center of the second support.

The first and second supports are preferably D-shaped. Such shape would conform to the shape of the atrial valve annulus and is therefore especially useful for treatment of atrial valves.

The first and second supports may each have an inner core covered by an outer layer, said inner core being formed from a more rigid material than said outer layer. The inner core may be formed from a metallic material, whereas the outer core may be formed from a fabric material. This implies that the surface of the support in contact with the valve tissue is soft to diminish the risk of rupture of the leaflets, whereas the support has a rigid shape which is maintained to retain a changed shape of the valve.

Alternatively, the first and second supports may be formed from a shape memory material. This implies that the supports may assume a desired, predetermined shape when inserted into position and maintain this shape.

The device may further comprise a plurality of fasteners arranged to extend between said first and second supports when the supports are placed on opposite sides of the heart valve. The fasteners would then serve to fix the position of the supports to each other and to the valve.

The first and second supports may comprise bores for receiving said fasteners therethrough. Thus, the positioning of the fasteners in the supports is predetermined for accomplishing a secure fixation.

The device may further comprise a removable material on at least one of said first and second supports for reducing friction between the respective supports and the valve tissue during initial engagement therewith, said material being removable to increase the friction during securement of the device to the valve tissue. The removable material provides a reduced friction which facilitates the guiding of the supports into abutment with the valve tissue and, when properly positioned, removing the removable material provides an increased friction that will serve to retain the relative position of the support and the valve tissue.

The opposed surfaces of the first and second supports may be roughened to facilitate engagement with the valve tissue. The opposed surfaces may be roughened in a pattern extending along the longitudinal direction of the rings. This implies that the roughened surface will serve to prevent slippage of tissue through the pinch of the supports while presenting a low friction for the supports to be turned into position abutting the valve.

According to a second aspect of the invention, there is provided a kit for improving the function of a heart valve comprised of valve tissue including an annulus and a plurality of leaflets. The kit comprises a first loop-shaped support, which is configured to abut a first side of the heart valve, a second loop-shaped support, which is configured to abut a second side of the heart valve opposite to said first side, whereby a portion of the valve tissue is trapped between the first and second supports. The kit further comprises at least one fastener for connecting the first and second supports when arranged in engagement with the heart valve.

The kit may be used to perform annuloplasty, that is to reshape the valve annulus, in order to improve the function of the valve. The kit comprises first and second loop-shaped supports, which are to be positioned on opposite sides of the heart valve, and fasteners, which connect the supports and fixate them to each other and to the valve tissue. As a result, valve tissue will be trapped between the supports to fixate a desired shape of the valve. The first and second supports are separate entities which may be separately placed on opposite sides of the heart valve. This implies that while the first and second supports may over time grow into the valve tissue, the kit does not present any surface of foreign material that may cause blood clot forming or tissue overgrowth in the opening of the heart valve.

The first and second supports may comprise receiving members for receiving said at least one fastener. The location of the receiving members at the first and second supports will then determine the relationship between the first and second supports that will be fixated by the fasteners.

The at least one fastener may be arranged on the first support and the second support may comprise receiving members for receiving said at least one fastener. As a result, the kit consists of fewer parts and the fasteners may be introduced into a patient together with the first support.

The at least one fastener may comprise a sharp projection for penetrating valve tissue. This facilitates positioning of the fastener in the patient, since a relatively small force is needed for pushing the fastener through the valve tisse.

The supports may be formed from a magnetic material such that the supports when being introduced on opposite sides of the heart valve may be subject to a magnetic field to attract the supports towards each other for temporarily fixating them on the opposite sides of the heart valve. In this way, the interrelationship of the supports may be at least temporarily fixated without the need of fasteners penetrating valve tissue. Thus, the positions of the supports may be temporarily fixated while the positions are secured by fasteners.

According to a third aspect of the invention, there is provided a device for improving the function of a heart valve comprised of valve tissue including an annulus and a plurality of leaflets. The device comprises a first loop-shaped support, which is configured to abut a first side of the heart valve, a second loop-shaped support, which is configured to abut a second side of the heart valve opposite to said first side, whereby a portion of the valve tissue is trapped between the first and second supports, and a connecting part for connecting an end of the first loop-shaped support to an end of the second loop-shaped support such that the supports and the connecting part form a coil-shape.

The device may be used to perform annuloplasty, that is to reshape the valve annulus, in order to improve the function of the valve. The device comprises first and second loop-shaped supports, which are to be positioned on opposite sides of the heart valve, and a connecting part, which connect the supports such that a coil-shape is formed. As a result, the coil-shape may be applied at a commissure between the leaflets of the heart valve and be rotated 360° such that one loop-shaped support is inserted through the commissure to extend along one side of the valve and the other loop-shaped support is arranged along the opposite side of the valve. Thus, © valve tissue will be trapped between the supports to fixate a desired shape of the valve.

The connecting part may be releasably attached to at least one of the first and second loop-shaped supports for disconnecting the end of the first loop-shaped support from the end of the second loop-shaped support after insertion to the heart valve.

This implies that the device may be placed in abutment with the heart valve without having any part extending through the opening of the heart valve. Thus, the first and second supports may separately be arranged in abutment with valve tissue such that the each support may over time grow into the valve tissue. As a result, the device does not present any surface of foreign material that may cause blood clot forming or tissue overgrowth in the opening of the heart valve.

The device may further comprise a carrier removably coupled to the supports for carrying the supports to the heart valve, wherein the connecting part is attached to the carrier such that the connecting part may be removed with the carrier after the supports have been placed in engagement with valve tissue. As a result, the supports may be easily applied at the heart valve by rotating the coil-shaped member. After the insertion of the supports, the connecting part may be removed such that the implanted device does not present any surface of foreign material that may cause blood clot forming or tissue overgrowth in the opening of the heart valve.

BRIEF DESCRIPTION OF THE DRAWINGS

The invention will now be described in further detail by way of example under reference to the accompanying drawings.

DETAILED DESCRIPTION OF A PREFERRED EMBODIMENT

Figure 1:
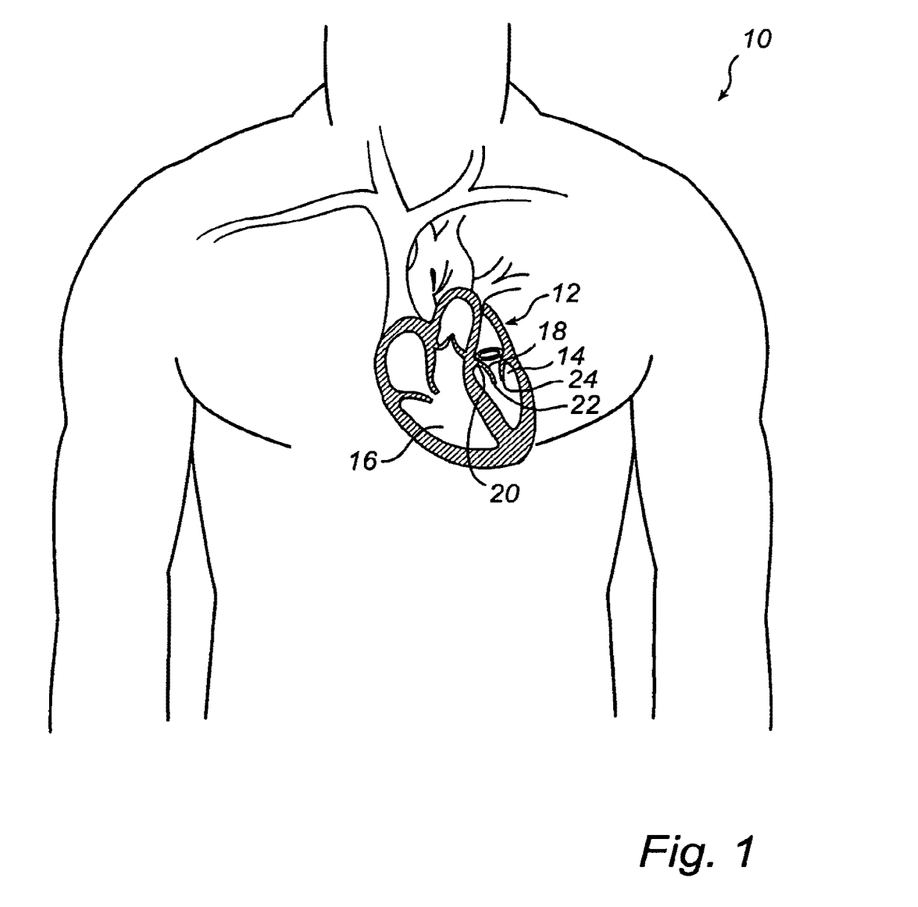
FIG. 1 schematically illustrates a patient with a heart shown in cross-section and a device of the present invention schematically illustrated as supporting the mitral valve.
Figure 1A:
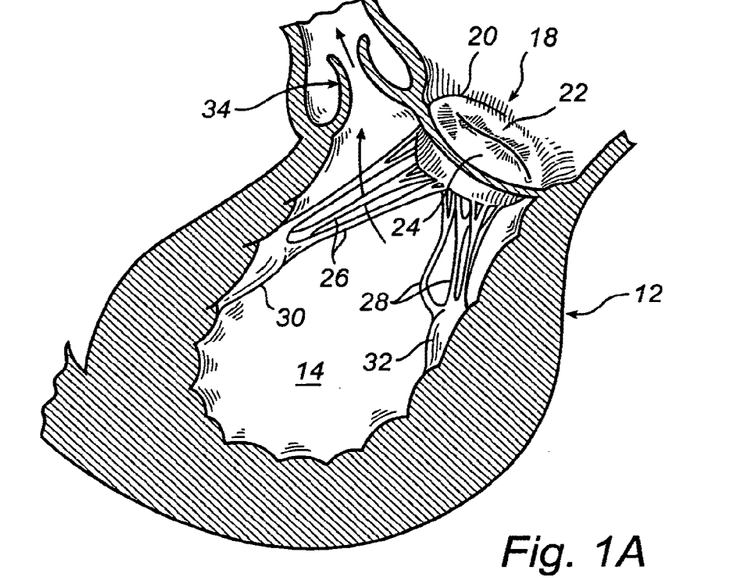
FIG. 1A is a cross-sectional view of the left ventricle showing the mitral valve and a device of the invention in perspective.

FIG. 1 illustrates a patient 10 having a heart 12 shown in cross-section including a left ventricle 14 and a right ventricle 16. The concepts of the present invention are suitable to be applied, for example, to a mitral valve 18 which supplies blood into left ventricle 14. Mitral valve 18, as better shown in FIG. 1A, includes an annulus 20 and a pair of leaflets 22, 24 which selectively allow and prevent blood flow into left ventricle 14. It will be appreciated that the term valve tissue is used extensively throughout this disclosure in reference to the drawings. The inventive principles are equally applicable when referring to any valve tissue such as annulus tissue, leaflet tissue or other attached vessel tissue. Leaflets 22, 24 are supported for coaptation by chordae tendinae or chords 26, 28 extending upwardly from respective papillary muscles 30, 32. Blood enters left ventricle 14 through mitral valve 18 and is expelled during subsequent contraction of heart 12 through aortic valve 34. It will be appreciated that the present invention is applicable to tricuspidal heart valves as well.

Figure 2:
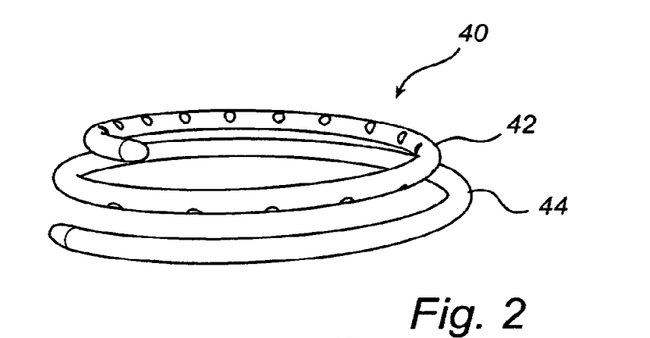
FIG. 2 is a perspective view of a device according to an embodiment of the invention.
Figure 3:
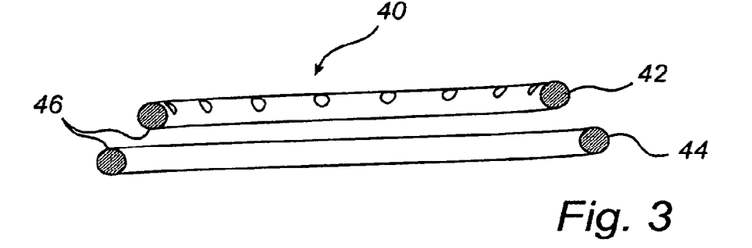
FIG. 3 is a cross-sectional view of the device in FIG. 2.
Figure 4A:
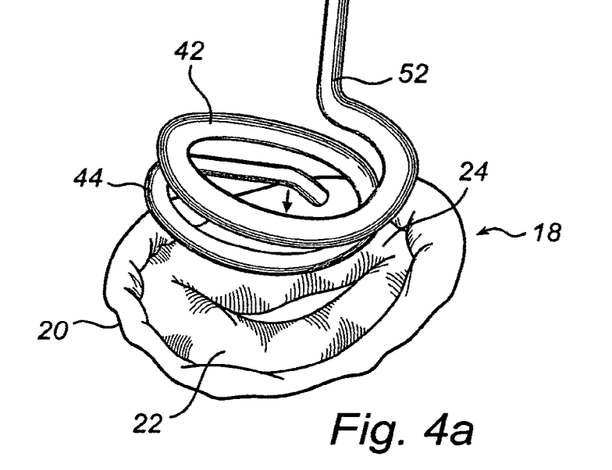
FIGS. 4a-b are partially sectioned perspective views of the mitral valve and the device of the invention during implantation of an annuloplasty implant of the device.
Figure 4B:
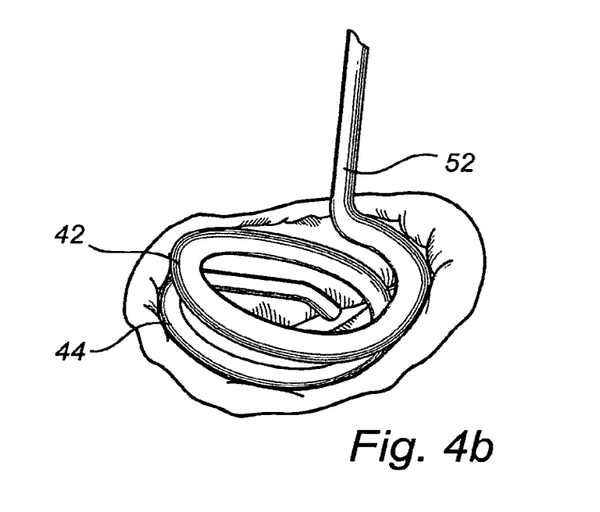

A device 40 according to a first embodiment of the present invention is shown in FIGS. 2 and 3. The device comprises a first and a second loop-shaped support 42, 44. The first support 42 is continuous with the second support 44 such that the supports 42, 44 assume a coiled configuration in the form of a spiral or keyring-type configuration with two loops. Any suitable medical grade material(s), such as medical grade metals or plastics, may be used to form the device 40.

The second support has an outer boundary which is greater than the outer boundary of the first support. The supports have corresponding shapes with the second support being in larger scale than the first support. This is advantageous in creating a pinch of the valve tissue between the first and second supports, as will be described below with reference to FIG. 7. An end of the second support, which will lead the coil during insertion of the device at the valve, has a greater pitch than the rest of the coil. This implies that the leading end of the coil during rotation into position in the valve will project from immediate contact with the valve tissue and, therefore, the risk that the coil is caught by the chords is diminished.

The device 40 is shown in cross-section in FIG. 3. The device 40 has a round cross-sectional shape. The opposed surfaces 46 provide a pinch to trap valve tissue therebetween. The round cross-section is also advantageous in creating a pinch of the valve tissue which will not harm the leaflets in their movement during normal heart action, as will be further described below with reference to FIG. 7.

The device 40 may be formed from a core of a rigid material, such as a metal, e.g. titanium, or plastic. The rigid material may provide a passive spring function such that the loops of the coil may be forced a small distance away from each other but will flex back towards each other when the force is released. The core of the device 40 may be coated by a softer layer, such as a textile.

The device 40 may alternatively be formed from a shape memory material. The device 40 will then assume a desired, programmed shape, when e.g. heated to a specific temperature. This allows the device 40 to be compressed during insertion and to assume a spiral shape when inserted at the heart valve.

Figure 5:
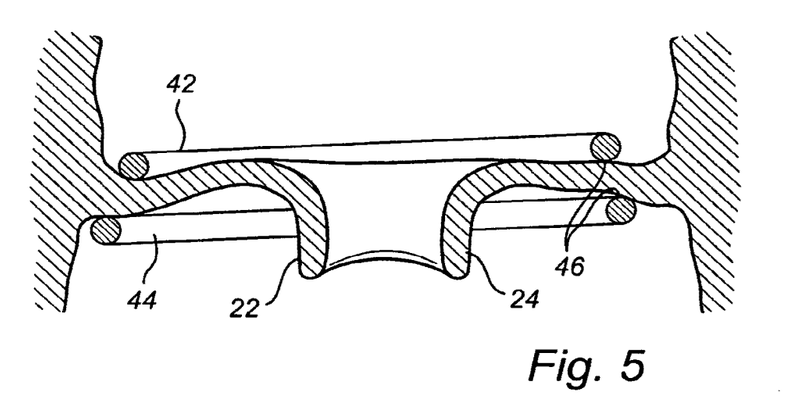
FIG. 5 is a partially sectioned perspective view showing the device of the invention when the implantation instrument has been turned into position.

Referring now to FIGS. 4-7, a method for repairing a heart valve by means of the device will be described. First, access to the heart valve is achieved by conventional techniques, including arresting the heart and opening the chest. In FIG. 4*a*, the device is shown when being inserted to the mitral valve 18. The device 40 is being carried on a carrier 52, which is connected to a stem for remote control of the positioning of the carrier 52. An end of the second loop-shaped support 44 is brought to the opening of the mitral valve 18 at a commissure between the leaflets 22, 24, as shown in FIG. 4*b*. The end is led through the opening and the carrier 52 is turned 360 degrees. Thus, the second support 44 will be rotated into place on one side of the valve 18, whereas the first support 42 is placed on the opposite side of the valve 18. In this way, the device 40 is arranged in engagement with the valve 18, as shown in FIG. 5.

Figure 10A:
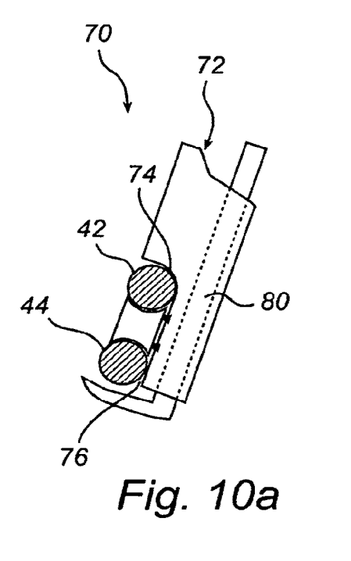
FIG. 10a is a side view of a carrier portion of an insertion instrument engaging the device of the invention.
Figure 10B:
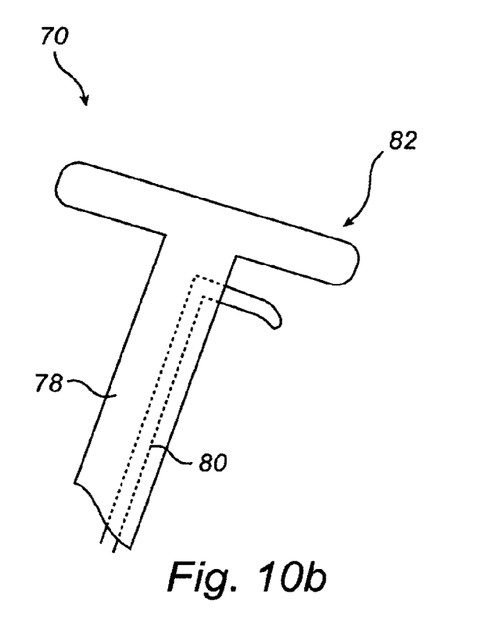
FIG. 10b is a side view of a handle portion of the insertion instrument.
Figure 10C:
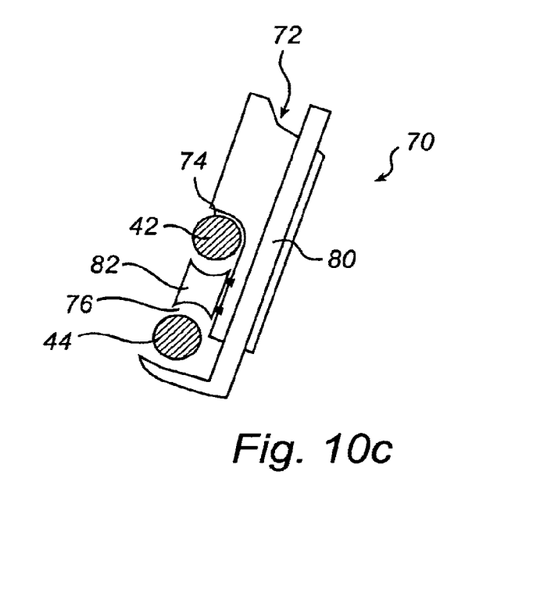
FIG. 10c is a side view of the carrier portion of the insertion instrument showing the device of the invention being released.

Referring now to FIGS. 10*a-d*, an insertion instrument 70 for inserting the device will be described in more detail. The insertion instrument 70 comprises a carrier 72, which is arranged to receive a portion of the first and second supports 42, 44, respectively, in grooves 74, 76, as shown in FIG. 10*a*. The carrier 72 is connected to a stem 78 for remote control of the supports 42, 44. An arm 80 is arranged along the stem 78 and engages the lower support 44. The stem 78 and the arm 80 end in handle 82 for remote control, as shown in FIG. 10*b*. The supports 42, 44 may be positioned on opposite sides of the valve by turning the stem 360 degrees. The arm 80 may be moved downwards for releasing the lower support 44, as shown in FIG. 10*c*. When the arm 80 is moved downwards, a mid portion 82 of the carrier 72 between the grooves 74, 76 is also moved downwards for releasing the upper support 46.

The supports 42, 44 are now placed on opposite sides of the valve 18 pinching valve tissue therebetween to maintain a shape of the valve 18. The leaflets 22, 24 may now be drawn towards each other through the pinch of the support rings 42, 44 so as to remodel the shape of the valve 18. The leaflets may be drawn through the pinch by means of a forceps instrument. The supports 42, 44 may flex away from each other to allow drawing leaflets 22, 24 through the pinch and towards each other for preventing the leaflets 22, 24 to slip back. The valve annulus 20 may in this way be remodelled and the new shape is maintained by the supports 42, 44. The supports 42, 44 may have roughened, opposed surfaces 46 to better keep the leaflets 22, 24 from slipping through the pinch and to hold the valve annulus 20 in its reshaped form.

Figure 6A:
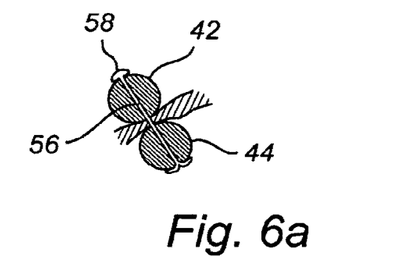
FIG. 6 is a perspective view showing the device after implantation is completed.
Figure 6B:
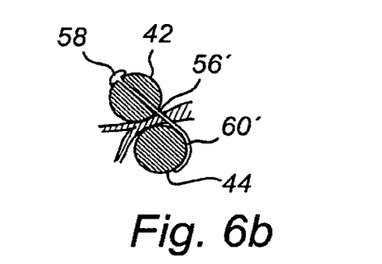

The device 40 may now be secured to the valve 18 for strengthening the fixation of the relative position between the supports 42, 44 and the valve tissue. The supports 42, 44 may comprise respective bores 54 through the opposed supports for receiving separate fasteners 56. The fasteners 56 may be threaded or unthreaded pins and may be pushed into position extending through bores in both supports and valve tissue therebetween. The fastener may have an end 58 with larger diameter than the bores 54 such that the fastener 56 may not fall through the bore 54. In this way, the device 40 is firmly attached to the valve 18 for keeping the valve annulus 20 in its reshaped form, as illustrated in FIG. 6*a*. Many alternative embodiments of the fasteners may be contemplated. As shown in FIG. 6*a*, the fasteners 56 may have an end 60 with an expandable diameter for securing the fastener 56 after it has been pushed through the bores 54. Alternatively, the fastener 56' may have a curved portion 60' for gripping around one of the supports, such that the fastener 56' may extend through a bore 54 in one support and around the other support, as illustrated in FIG. 6*b*. As further alternatives, the fasteners may be clips, sutures, or projections that are extendable from at least one of the supports for engaging the valve tissue.

Figure 7:
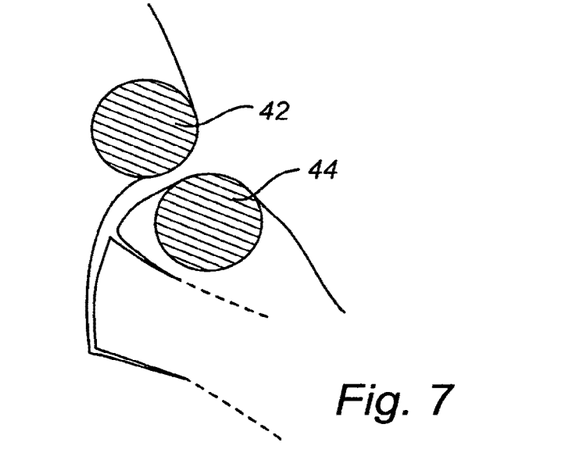
FIG. 7 is a cross-sectional view of the implanted device in FIG. 6.

As illustrated in FIG. 7, the second support 44 is slightly displaced radially with respect to the first support 42. This implies that the first and second supports 42, 44 are not arranged directly on top of each other. The pinch between the first and second supports is therefore not sharply defined in a radial direction of the valve. This implies that a pinching force between the supports is not focussed to a specific radial position of the valve. As a result, the pinching force does not affect the movement of the leaflets during normal heart action and there is a diminished risk of rupture in the leaflets at the pinch. The supports are interrelated in such manner that the outer boundary of the first support 42 has a diameter corresponding to a line through the center of the second support 44. Thus, the supports 42, 44 overlap somewhat such that tissue is not allowed to move through the pinch and the shape of the valve is maintained. Further, the cross-section of the supports 42, 44 is round, which also gives a soft contact between the supports and the valve tissue to further diminish the risk of rupture in the leaflets.

Figure 8:
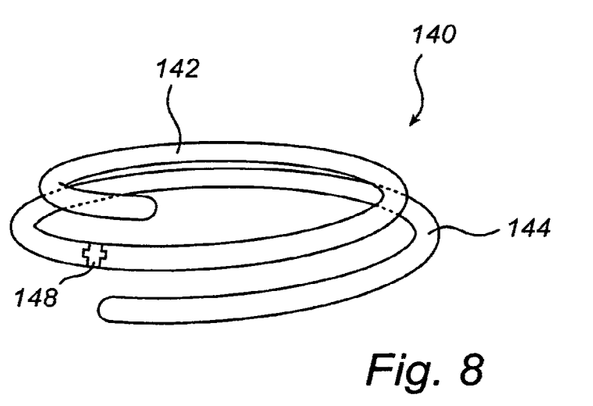
FIG. 8 is a perspective view of a device according to another embodiment of the invention.

Referring now to FIG. 8, another embodiment of the device 140 is described. The device 140 comprises a first and a second loop-shaped support 142, 144, which are connected to each other by means of a connecting part 148 so as to form a coil-shape. The coil-shape of the device is advantageous during insertion, since the device 140 may then be rotated into position, as described above. However, the connecting part 148 is detachable from at least one of the supports. Thus, when the device 140 has been inserted, the connecting part 148 may be detached and removed from the opening of the valve. If detachable from only one of the supports, the connecting part 148 may be arranged along the other support to make contact with valve tissue such as to be overgrown. However, the connecting part 148 is preferably detachable from both supports, whereby it may be removed from the patient after the device 140 has been inserted. The removal of the connecting part 148 from the opening of the valve implies that the device 140 does not present any surface of foreign material that may cause blood clot forming or tissue overgrowth in the opening of the heart valve. The connecting part 148 may be attached to an insertion instrument so that it-may easily be removed from the patient after being detached from the supports. The device 140 may advantageously be inserted using the insertion instrument 70 described above.

Figure 9:
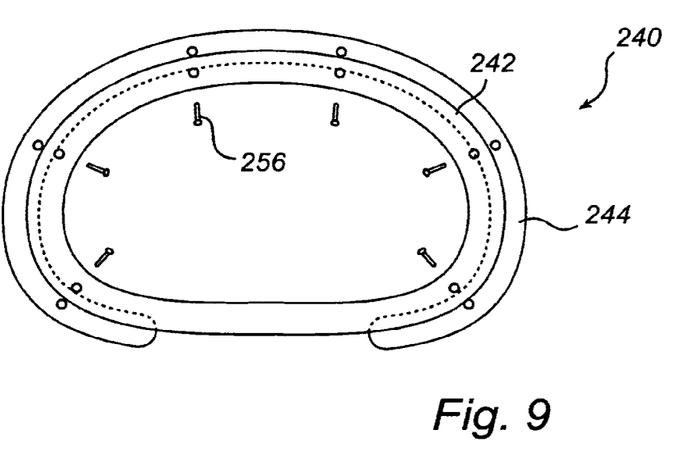
FIG. 9 is a perspective view of a kit according to a further embodiment of the invention.

Referring now to FIG. 9, a kit 240 according to a further embodiment of the invention will be described. The kit 240 comprises a first loop-shaped support 242 and a second loop-shaped support 244. The loop-shaped supports 242, 244 are separate entities. As a result, when the supports 242, 244 are inserted into a patient, no surface of foreign material that may cause blood clot forming or tissue overgrowth will be presented in the opening of the heart valve. The supports 242, 244 may be formed from or comprise a magnetic material. Thus, the supports 242, 244 may be subject to a magnetic force during insertion so as to temporarily connect the supports to each other. As a result, the supports 242, 244 may be rotated into position as described above, while the magnetic force would press the supports 242, 244 towards each other on opposite sides of the valve. One of the supports 244 is preferably open, e.g. C-shaped, such that the support 244 presents an end to lead the movement of the support 244 when being rotated into position. The kit 240 further comprises fasteners 256 to secure the position of the supports 242, 244. After the position of the supports have been secured, the magnetic force may be turned off leaving the supports in the patient.

It should be emphasized that the preferred embodiments described herein are in no way limiting and that many alternative embodiments are possible within the scope of protection defined by the appended claims.

For example, the access to the heart valve may be achieved endoscopically. In such case, the device 40 needs to be inserted through a narrow tube (endoscope). This implies that the device 40 will need to be compressed during insertion in order to pass through the endoscope. The device 40 needs to assume its proper shape after having been passed through the endoscope. Therefore, using an endoscopic approach, the device 40 should preferably be formed from a shape memory material. This allows the device 40 to be compressed and also to have a stable shape when being applied to the heart valve. As a further alternative, the access to the heart valve may be achieved through a catheter, which is passed through the vascular system to the heart. In this case, the supports may be formed from a shape-memory material, which during insertion extends along the catheter in a flexible state and, when pushed out of the catheter at the heart valve, assumes a prestressed coil-shape in order to abut the heart valve on opposite sides.

Many different shapes may be contemplated for the loop-shaped supports. For example, the supports may have elliptical, circular or D-shaped forms. One or both supports need not make an angular turn of 360° such as to have a C- or U-shape instead.

What is claimed is:

1. A heart valve annuloplasty system for improving the function of a heart valve comprising:
    a first loop-shaped support, which is configured to abut a first side of said heart valve,
    a second loop-shaped support, which is configured to abut a second side of said heart valve opposite to said first side such that said heart valve is trapped between said first looped-shaped support and said second loop-shaped support;
    said second loop-shaped support having an outer boundary which is greater than an outer boundary of said first loop-shaped support
    said first loop-shaped support and said second loop-shaped support each being formed from a magnetic material, such that, when subjected to an externally applied magnetic field, said first loop-shaped support and said second loop-shaped support, when arranged on radially displaced opposing sides of the heart valve, are attracted to each other by said magnetic field for holding said first loop-shaped support and said second loop-shaped support on opposing sides of the heart valve.

2. The system according to claim 1, comprising at least one fastener for connecting said first loop-shaped support and said second loop-shaped support together when arranged on opposite sides of said heart valve.

3. The system according to claim 2, wherein the first loop-shaped support and said second loop-shaped support comprise receiving members for receiving said at least one fastener.

4. The system according to claim 2, wherein said at least one fastener is disposed on said first loop-shaped support and the second loop-shaped support includes receiving members for receiving said at least one fastener.

5. The system according to claim 2, wherein said at least one fastener has a sharp projection for penetrating tissue of said heart valve.

6. The system according to claim 2, wherein said at least one fastener has an end of an expanded diameter.

7. The system according to claim 2, wherein said at least one fastener has a curved portion.

8. The system according to claim 1, wherein at least one of said first loop-shaped support and said second loop-shaped support is open.

9. The system according to claim 8, wherein said at least one of said first loop-shaped support and said second loop-shaped supports is C-shaped.

10. The system according to claim 1, wherein said first loop-shaped support and the second loop-shaped supports are separate and distinct units.

11. The system according to claim 1, wherein the first loop-shaped support is continuous with the second loop-shaped support.

12. The system according to claim 1, wherein said magnetic field is operative for being turned off.

13. A heart valve annuloplasty system for improving the function of a heart valve comprising:
    a first curve-shaped support, which is configured to contact a first side of said heart valve,
    a second curve-shaped support, which is configured to contact a second side of said heart valve opposite to said first side such that said heart valve is trapped between said first curve-shaped support and said second curve-shaped d support;

said second curve-shaped support having an outer boundary which is greater than an outer boundary of said first curve-shaped support said first curve-shaped support and said second curve-shaped support each being formed from a magnetic material, such that, when subjected to an externally applied magnetic field, said first support and said second support, when arranged on radially displaced opposing sides of the heart valve, attract said first curve-shaped support and said second curve-shaped support towards each other for holding said first curve-shaped support and said second curve-shaped on opposing sides of the heart valve;

wherein said applied magnetic field is operative for being turned off.

* * * * *